US005343261A

United States Patent [19]

Wilson

[11] Patent Number: 5,343,261

[45] Date of Patent: Aug. 30, 1994

[54] DEVICE FOR INDUCING SACCADIC EYE MOVEMENT

[76] Inventor: David L. Wilson, 616 Azalea, Redding, Calif. 96002

[21] Appl. No.: 818,355

[22] Filed: Jan. 9, 1992

[51] Int. Cl.[5] .......... A61B 3/00

[52] U.S. Cl. .......... 351/203; 351/222; 351/224

[58] Field of Search .......... 351/210, 211, 212, 221, 351/224, 209, 225, 226, 203, 222, 223

[56] References Cited

U.S. PATENT DOCUMENTS

| | | | |
|---|---|---|---|
| 4,421,393 | 12/1983 | Cohen et al. | 351/224 |
| 4,818,097 | 4/1989 | Linde | 351/224 |
| 4,850,691 | 7/1989 | Gardner et al. | 351/210 |
| 4,854,694 | 8/1989 | Hirano et al. | 351/224 |
| 5,094,521 | 3/1992 | Jolson et al. | 351/210 |

OTHER PUBLICATIONS

Eye Movement Desensitization: A New Treatment for Post–Traumatic Stress Disorder By: Francine Shapiro; J. Behav. Ther. & Exp. Psychiat. vol. 20, No. 3, pp. 211–217 1989.

*Primary Examiner*—William L. Sikes
*Assistant Examiner*—Hung Xuan Dang
*Attorney, Agent, or Firm*—Bielen, Peterson & Lampe

[57] ABSTRACT

A device for inducing saccadic eye movement in a subject utilizing a source of power which activates a multiplicity of visual signaling elements. The visual signaling elements are mounted in a structure such that the elements are placed at a certain level and angle relative to the eye or eyes of the subject. The visual signaling elements are sequentially activated in a back and forth manner.

10 Claims, 2 Drawing Sheets

DEVICE FOR INDUCING SACCADIC EYE MOVEMENT

BACKGROUND OF THE INVENTION

The present invention relates to a device for inducing saccadic eye movement in a subject.

Post-traumatic stress disorder (PTSD) is generally characterized by anxiety attacks, sleep disturbances, flashbacks, and other symptoms which relate to a prior traumatic event. PTSD is particularly common to physical and sexual assault victims and war veterans.

Prior treatments for PTSD have included "systematic desensitization" and "flooding". These prior techniques have met with only limited success.

Reference is made to an article entitled "Eye Movement Desensitization: A New Treatment For Post-Traumatic Stress Disorder" by F. Shapiro. In this article, a new technique for the treatment of PTSD is described in which the patients are instructed to visualize the traumatic event, identify negative thoughts, concentrate on the physical sensations of the anxiety, and visually track the therapist's hand, with index and middle finger raised, while the hand is moved in a back and forth motion. The latter step involves the therapists moving his or her fingers rhythmically along the line of vision of the patient. Before, during, and after such technique, clients are then measured for a self-reported level of anxiety. It has been found that inducement of such saccadic eye movement as described above has been very successful in treating cases of PTSD, and other trauma-based disorders.

Unfortunately, control of the speed and path of the therapist's fingers is difficult to achieve, and a jerky eye movement has a tendency to induce stress in the patient while a rhythmic eye movement produces the opposite result. In addition, application of the Eye Movement Desensitization and Reprocessing technique (EMDR) to multiple successive subjects described above tires the therapist's arm and seriously jeopardizes the consistency in the EMDR treatment. Further, the therapist may find it difficult to observe the subject's eye movement while maintaining a smooth rhythmic finger movement.

A device which permits a therapist to easily administer the Eye Movement Desensitization technique would represent a great advance in the medical field.

SUMMARY OF THE INVENTION

In accordance with the present invention a novel and useful device for inducing saccadic eye movement in a subject is herein provided.

The device of the present invention utilizes a source of power which may be electrical or mechanical. The source of power is used to activate a multiplicity of visual signaling elements which are arranged in a predetermined pattern. Where the signaling elements are lights, the source of power may be electrical. In many cases, the predetermined pattern for the signaling elements is a straight line.

The mounting structure for the visual signaling elements is also provided in the present invention. The mounting structure places the visual signaling elements at a certain level relative to the eye or eyes of the subject. To achieve this purpose, the mounting structure may include a bar having the visual signaling elements held to the same in such predetermined pattern. A post is connected the bar and may include a telescoping structure such that the height of the post is adjustable above a base. In addition, the bar having the visual signaling elements may rotate about the axis of the bar to present the visual signaling elements at a different angle relative to the plane of the subject's eyes. It should be noted that the base includes a housing for the various electrical and mechanical components of the device of the present invention. The visual signaling elements may be formed of light emitting diodes (LEDS). In this case, the source of power may be AC line electrical power or DC battery power.

Means is also included in the present invention for sequentially activating each of the visual signaling elements. Such means may take the form of a variable speed LED chaser mounted in the base portion of the device. A manual control knob may be held to the base for access by the operator of the device. In addition, the activation of the visual signaling elements may be tracked by a counter. Thus, the operator of the device may control the duration of the activation of the visual signaling elements. In addition, the rate of activation of the visual signaling elements may also be observed and determined by the user. The effect of the device of the present invention on the subject may be assessed by self report or other known stress measuring devices.

An audio signaling element may be included in the present invention for periodic activation of the same relative to the period of activation of the visual signaling elements. For example, an audio signal may be activated after completion of a sequence of visual signal elements. Such audio signaling elements may take the form of headphones placed on the patient for alternating tones between the left and right ears.

It may be apparent that a novel and useful device for inducing saccadic eye movement in a subject has been described.

It is therefor an object of the present invention to provide a device for inducing saccadic eye movement in a subject which is useful in the treatment of post-traumatic stress disorder (PTSD) and other trauma and anxiety-based emotional disorders, such as but not limited to phobias, panic disorder, generalized anxiety disorders, and the like.

It is another object of the present invention to provide a device for inducing saccadic eye movement in a subject which is usable in conjunction with physiological measuring devices such as polygraphs, monitoring respiration, heart rate, blood pressure, skin temperature, and the Galvanic Skin Response (GSR) .

Another object of the present invention is to provide a device for inducing saccadic eye movement in a subject which includes a multiplicity of visual signals which are sequentially operated at a rate, duration, and angle of observation which is adjustable and predetermined by the user.

Another object of the present invention is to provide a device for inducing saccadic eye movement in a subject in the treatment of post traumatic stress disorder which permits the therapist to observe the subject, especially the eye movement of the same.

Another object of the present invention is to provide a device for inducing saccadic eye movement in a subject which sequentially operates a series of visual signals in a particular pattern which are consistent and reliable.

The invention possesses other objects and advantages especially as concerns particular characteristics and features thereof which will become apparent as the specification continues.

DESCRIPTION OF THE DRAWINGS

FIG. 2A is a sectional view taken along line 2A—2A of FIG. 2.

Figure 1:
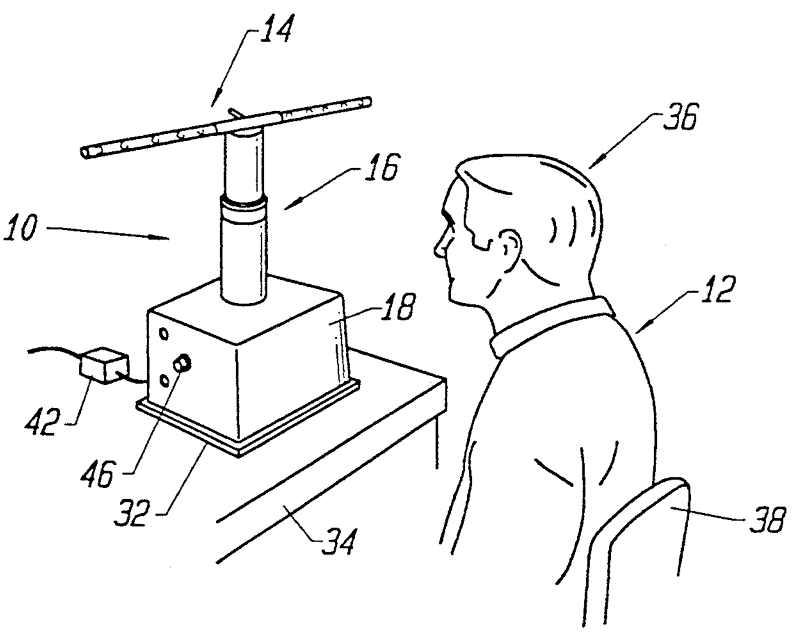
FIG. 1 is a top right perspective view of the device in use with a subject.

For a better understanding of the invention reference is made to the following detailed description of the preferred embodiments thereof which should be referenced to the hereinabove described drawings.

DESCRIPTION OF THE PREFERRED EMBODIMENTS

Various aspects of the present invention will evolve from the following detailed description of the preferred embodiments which should be taken in conjunction with the prior described drawings.

The invention as a whole is shown in the drawings by reference character 10. The device 10 is intended to induce saccadic eye movement in subject 12, FIG. 1. Device 10 includes as one of its elements a multiplicity of visual signaling elements 14 which are arranged in a predetermined pattern.

As depicted in the drawings, visual signaling elements 14 extend in substantially linear fashion. Visual signaling elements 14 are supported by mounting structure 16, best shown in FIGS. 2 and 3, which includes a base 18, bar 20, and a telescoping structure 22, therebetween. Telescoping structure 22 includes a T-shaped mount 24, hollow post 26, and compression ring 28 which fixes the extension of T-shaped mount 24 into hollow post 26 and, thus, fixes the height of bar 20 above base 18, directional arrow 30. Light bar 20 and visual signaling elements 14 relative to T-shaped mount 24, directional arrows 31 and 33, FIGS. 2A and 3, such that visual signaling elements 14 trace an arcuate path. Set screw 35 fixes the position of light bar 20 relative to T-shaped mount 24. As depicted in FIG. 1, base 18 includes a lower plate 32 to aid in the selective placement of device 10 on a platform such as table 34, FIG. 1. Bar 20 and plurality of visual signaling elements 14 may be placed at, above, or below eye level, or at an angle to the horizontal plane of the eyes of subject 36 seated in chair 38, FIG. 1, as determined by the operator of device 10. Thus, device 10 allows for adjustment of light bar 20 horizontally, vertically and angularly relative to subject 36.

Figure 2:
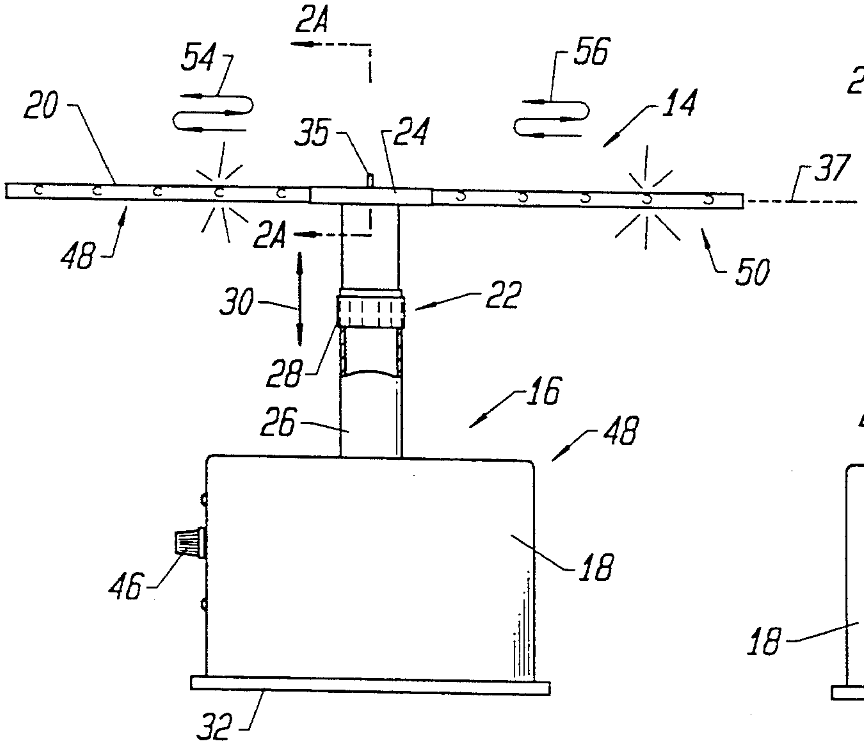
FIG. 2 is a side elevation view of the device of the present invention.
Figure 3:
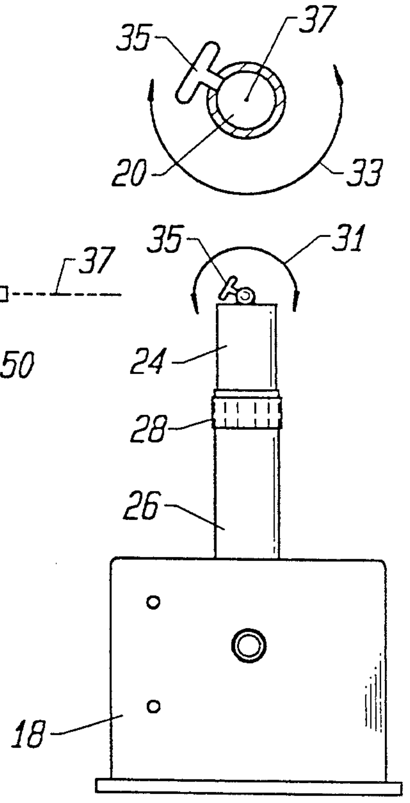
FIG. 3 is a front elevational view of the device of the present invention.

Multiplicity of visual signaling elements 14 may take the form of light emitting diodes (LEDS). Such LEDS are activated by a source of power 40 which may be line AC power rectified to D.C. power. Power source 40 is passed through a rectifier 42 and into a controller 44 found within housing or base 18, FIG. 4. Controller 44 may be a variable speed LED chaser which is commercially available. Controller 44, thus, includes a knob 46 accessible from the outside of housing or base 18. Controller 44 permits the subject or the person administering device 10 to change the speed of the LED chaser. With reference to FIG. 2, it may be apparent that two sets of LED's 48 and 50 are depicted on either side of T-shaped mount 24. Controller 44 serves as means 48 for sequentially activating each of the multiplicity of visual signaling elements 14. As depicted in FIG. 2, means 48 activates signaling element sets 48 and 50 such that sets 48 and 50 illuminate sequentially from left to right, from right to left, and again from right to left, etc. as long as controller 44 is in its active state, directional arrows 54 and 56.

Figure 4:
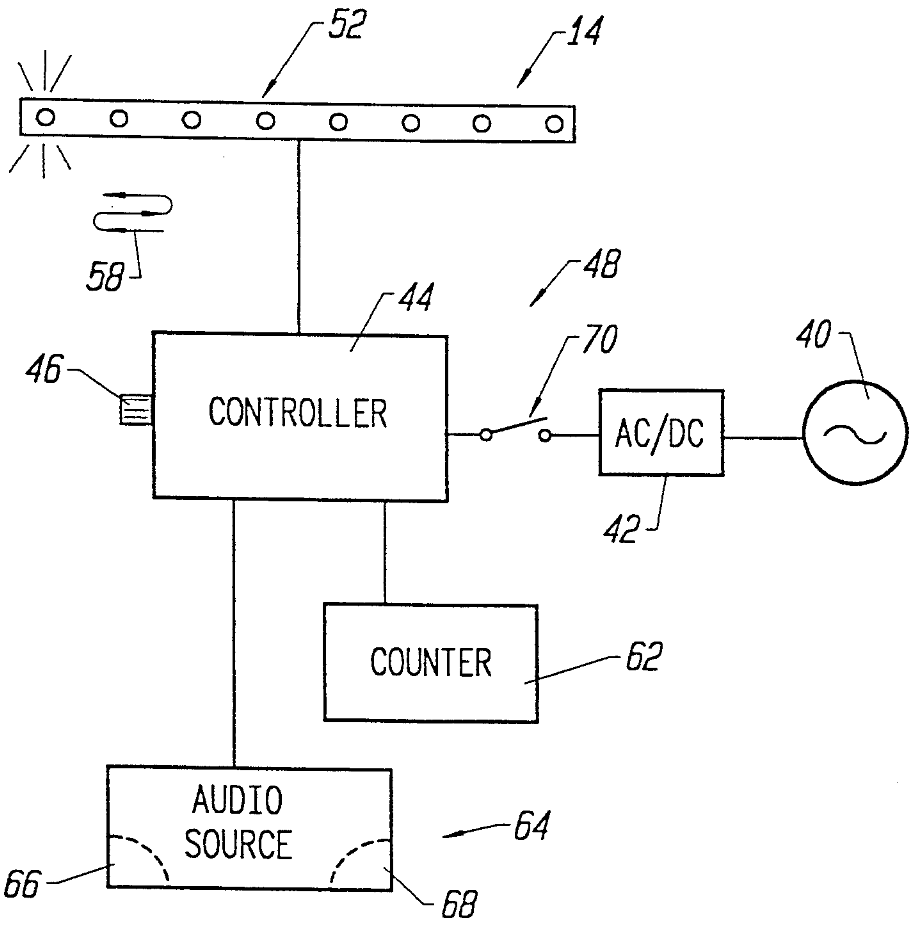
FIG. 4 is a schematic view depicting the electrical components of the device of the present invention.

With reference to FIG. 4, it may be observed that multiplicity of visual signaling elements 52 are in a single line rather than in the split configuration depicted in FIG. 2. Multiplicity of visual signaling elements (LEDS) 52 move back and forth across bar 14 according to representative directional arrow 58. It should be noted that other patterns of visual signaling elements may be employed as long as saccadic eye movement is induced in the subject 36.

Figure 5:
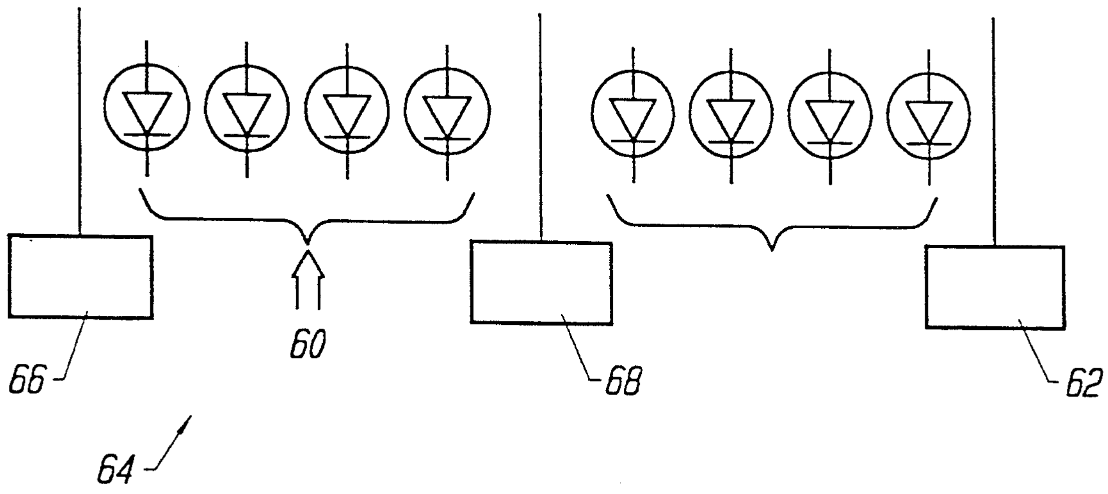
FIG. 5 is a detailed schematic view of the arrangement of the LED, counting, and audio signaling outputs of the controller of the present invention.

Controller 44 include the outputs, depicted in FIG. 5, shown by eight LED's 60. In each cycle, the eleven outputs depicted in FIG. 5, power the eight LEDS, a counter 62, and an audio source 64 may be in the form of left and right earphones 66 and 68 which may be placed on the subject 36. Thus, controller 44 is able to sequentially activate LED's 14 or 52 as well as an audio source 64.

The following table represents a list of components used in a system of the present invention:

TABLE I

| ITEM | SOURCE |
|---|---|
| 1. Controller 40 | Variable Speed LED CHASER-All Electronics Corp. Van Nuys, CA. |
| 2. Counter 62 | Electro Mechanical Counting Module 62-#279-222-Radio Shack Ft. Worth, Texas |
| 3. Rectifier 42 | 300MA, A5-501/AS 501k 1100AC to 12 vv DC Gemini Industries Clifton, N.J. |
| 4. Audio Source 64 | Catalogue 276-5013, page 28-Radio Shack Ft. Worth, Texas |
| 5. Bar 20 and LEDS 14 | Interior Night Runner Light No. 750, Ralley Accessory, Inc. Miami, Fl. |
| 6. Switch 70 | Toggle Switch SPST 3A, 125 V, Catalogue 275-602-Radio Shack Ft. Worth, Texas |

In operation, the subject 36 is placed in a sitting position in front device 10, FIG. 1. The person controlling device 10, usually a therapist, activates device 10 from power source 40. Switch 70 is then closed to permit DC power to travel to controller 44. Controller 44 then activates multiplicity of visual signaling elements or LEDS 14 or 52 in a sequential matter, i.e.: left to right, right to left etc. Controller 44 activates counter 62 during its output cycle such that movement to the right or left is recorded. In this manner, the therapist may track the number of saccadic eye movements and gage the same against the anxiety level of the subject 36, which is measured by self report or physiological measures know in the art. An audio source 64 may activate a left earphone 66 or right earphone 68 as depicted in FIG. 5 such that four LEDS sequentially flash, a first audio tone is sent to one ear, four LEDS sequentially flash, the second audio tone is sent to the other ear, and so forth. It has been found that device 10 serves as a substitution for therapist's hand inducement of saccadic eye movement, during EMDR treatment in clinical application and avoids the "tennis elbow" common among practitioners and researches in the art. Device 10 provides consistent, measurable speed at selected positions of observation (horizontal, vertical and angular) by subjects.

While in foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed:

1. A device for inducing saccadic eye movement in a subject, comprising:

a. a source of power;

b. a multiplicity of visual signaling elements arranged in a predetermined substantially linear alignment, said visual signaling elements being activated by said source of power;

c. a mounting structure for said visual signaling elements, said mounting structure placing said aligned visual signaling elements at a certain level relative to the eye of the subject; and d. means for sequentially and repeatedly activating each of said aligned visual signaling elements to produce a cyclic back and forth visual pattern.

2. The device of claim 1 in which said mounting structure includes a bar, said visual signaling elements being held to said bar in said predetermined pattern, and a post, said post extending upwardly from said base and being connected to said bar.

3. The device of claim 2 in which said mounting structure further includes means for adjusting the extension of said bar relative to said base.

4. The device of claim 3 in which said means for adjusting the extension of said bar relative to said base includes said post being constructed of first and second members, said first member being movable relative to said second member and means for fixing said relative movement between said first and second member.

5. The device of claim 3 which additionally includes means for angularly adjusting said visual signaling elements held to said bar.

6. The device of claim 1 which additionally comprises means for counting the activation of said visual signaling elements.

7. The device of claim 6 which additionally comprises an audio signaling element and means for periodically activating said audio signaling element during the time period of said activation of said visual signaling elements.

8. The device of claim 1 in which said visual signaling elements are light emitting diodes.

9. The device of claim 1 which additionally comprises means for determining the rate of activation of said visual signaling elements.

10. The device of claim 9 which additionally comprises a manually operated controller for operating said means for determining the rate of activation of said visual signaling elements.

* * * * *